United States Patent [19]

Votel

[11] Patent Number: 4,559,042
[45] Date of Patent: Dec. 17, 1985

[54] SAFETY ENCLOSURE FOR DISPOSABLE HYPODERMIC SYRINGE NEEDLE

[75] Inventor: Thomas W. Votel, St. Paul, Minn.

[73] Assignee: Comp Equipment Corporation, St. Paul, Minn.

[21] Appl. No.: 607,711

[22] Filed: Jan. 6, 1984

Related U.S. Application Data

[63] Continuation of Ser. No. 362,320, Mar. 26, 1982, abandoned.

[51] Int. Cl.⁴ .............................................. A61M 5/00
[52] U.S. Cl. .................................... 604/192; 604/263
[58] Field of Search ....................... 604/263, 197, 192

[56] References Cited

U.S. PATENT DOCUMENTS

| | | | |
|---|---|---|---|
| 1,179,560 | 4/1916 | Reed | 128/215 |
| 3,021,942 | 2/1962 | Hamilton | 128/218 N |
| 3,072,120 | 1/1963 | Sharp et al. | 128/215 |
| 3,130,742 | 4/1964 | Higgins et al. | 128/218 R |
| 3,401,693 | 9/1968 | Cohen | 128/221 |
| 3,796,218 | 3/1974 | Burke et al. | 128/221 |
| 4,270,536 | 6/1981 | Lemelson | 128/218 N |

Primary Examiner—John D. Yasko
Attorney, Agent, or Firm—Merchant, Gould, Smith, Edell, Welter & Schmidt

[57] ABSTRACT

An elongated tubular enclosure or receptacle has a radially outward extending shield for protecting the hand of the user when the disposable needle of a hypodermic syringe is being placed into the enclosure after use and before discarding.

6 Claims, 7 Drawing Figures

SAFETY ENCLOSURE FOR DISPOSABLE HYPODERMIC SYRINGE NEEDLE

This application is a continuation of application Ser. No. 362,320 filed Mar. 26, 1982 now abandoned.

FIELD OF THE INVENTION

This invention is for use in the medical field for the purpose of protecting the user of a disposable hypodermic syringe, such as a nurse, for example, after the syringe has been used and the needle is being inserted into a receptacle before disposal.

DESCRIPTION OF THE PRIOR ART

The prior art, which will be described later in somewhat greater detail, generally provides an elongated plastic hollow tube closed at one end which is slipped over the needle and fits snugly on the tapered end of the barrel when the syringe is first assembled and initially helps keep the needle sterile. The same tube may then be used to cover over the needle after the syringe has been used but before it is disposed. All too often a user either by carelessness, inattention or being distracted will miss the opening and stick himself or herself in a finger with the needle when inserting it into the tube. This is particularly hazardous because of the risk of hepatitis or resistant bacterial infection. Very frequently medication such as HBIG (Hyper Immune Gamma Globulin for Hepatitis B) has to be given to someone who has been accidentally stuck by a needle. This material is very expensive, for example, presently being about $70 per injection with two injections normally being required. This is still not a one hundred percent positive prevention so some significant risk still remains. If the needle is not covered over or placed in some safety enclosure, it is very possible that janitors or cleaning persons may be punctured while disposing trash or picking up laundry in which an unprotected or uncovered needle lies. As an example, it has been the inventor's experience that approximately 200,000 hypodermic syringes were used in one year at a hospital at which he was on staff and there were 120 needle puncture wounds reported that year. The great majority of these wounds occurred to nurses after they had used the needle on a patient while they were inserting the needle into a tube or the like for disposal but some are results or wounds to janitorial persons because the needle was not covered.

SUMMARY OF THE INVENTION

This invention provides an elongated receptacle or tube with safety shield extending radially outward near its open end to protect the fingers when the needle is being placed into the receptacle before disposal. The shield may be an integral part of the receptacle or it may be removably attached thereto. In one embodiment the shield is made out of some material strong enough to protect against the needle puncture but having some degree of resiliency of flexibility so that when the hypodermic syringe is initially assembled and placed in its normal package the shield can be squeezed or pressed down so as not to make the package unduly bulky but when the package is opened the shield springs out to provide the desired protection. In the case where the shield is removably attached to the safety receptacle the resiliency of the material is not important because the shield would be separate and would be slipped on the receptacle only after the needle has been used and just before it is discarded. The safety feature provided by this invention would add little if anything to the cost of hypodermic syringes and would more than compensate for any additional cost by virtually eliminating a health and safety hazard.

DESCRIPTION OF THE PREFERRED EMBODIMENT

Figure 1:
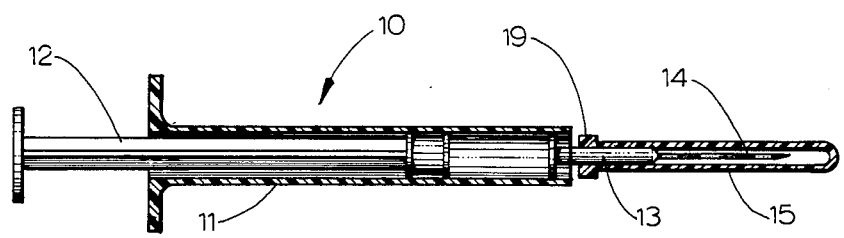
FIG. 1 illustrates prior art.

The conventional hypodermic syringe 10 generally consists of a molded plastic barrel 11 for holding fluid, a plunger 12 used to draw fluid into the barrel or to eject fluid, a needle holder 13 at one end of the barrel which is usually an integral part of the barrel itself and a hollow needle 14 through which the fluid passes into or out of the body of the patient or animal. To help keep the needle sterile before it is used, a small diameter elongated plastic tubular covering 15 having a small hub 19 near its open end and closed at its other end covering over the needle 14 is removably attached to barrel 11 near the needle holder area usually merely by a friction fit so it can be easily removed for use. Additionally, ordinarily each syringe assembly is separately enclosed in a container of some sort, usually a paper package, which can be easily opened when the syringe is to be used. After the package is opened and the syringe is being prepared for use tubular covering 15 is removed and the needle is injected. In some cases the syringe assembly remains intact but in other cases the barrel and the needle may be separated, for example, when the syringe is used to aspirate some part of the body. In any event, for safety reasons as described earlier, the nurse, for example, will place the needle into a receptacle before disposing it. If the needle is discarded uncovered into the waste it could later accidentally prick janitors or others who might be cleaning up. Also, if the needle is laying around uncovered, it could fall into bed sheets or other laundry and eventually stick someone. When the syringe remains intact, the nurse will usually insert the needle back into tube 15. If the needle is separated, the nurse may place the needle in the same receptacle or in a different one before throwing it away. As mentioned earlier, it is not uncommon for the user to be stuck by the needle while trying to place the needle into tube 15 or some other receptacle because the nurse fails to insert the needle into the receptacle opening and as a result, gets stuck by the point of the needle.

Figure 2:
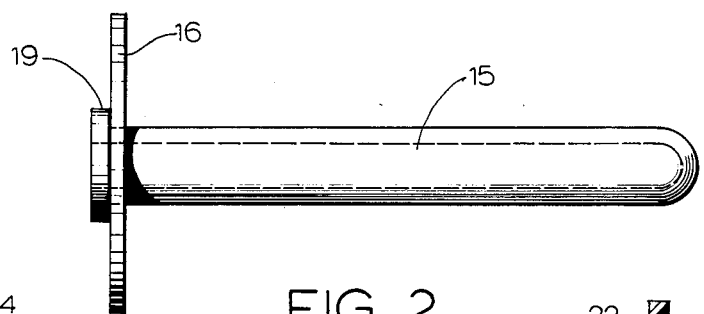
FIG. 2 illustrates an embodiment according to the teachings of this invention.
Figure 3:
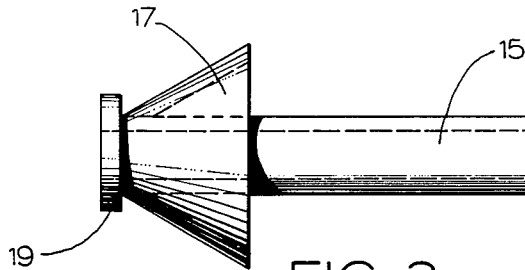
FIG. 3 illustrates another embodiment.

To overcome this problem, the present invention provides a shield near the open end of the receptacle. In one embodiment, the shield may be in the form of an annular disc 16 which is coaxial with the longitudinal axis of the receptacle and extends radially and perpendicular outward therefrom. The receptacle may be a different tube or may be tube 15 which had originally covered the needle. Disc 16 may be formed integrally with the tube 15 when it is molded or formed or it can be separately made and slipped over the tube and frictionally held in place or it may be locked into a slot around the tube near the open end. As a further feature, the disc 16 may be made out of material that is strong enough to not be torn or pierced by the needle point yet be somewhat flexible or resilient so that if it is made as an integral part of the tube 15, when the hypodermic syringe is first assembled the disc 16 can be folded or squeezed back on the tube and held in place when packaged yet spring back to its normal position as a shield when the package is opened. This avoids adding appreciable bulkiness to the packaging of the hypodermic syringe. An alternative embodiment is illustrated in FIG. 3 which shows a cone shaped shield which flares outward and rearward from the open end of tube 15. This also may be constructed as an integral part of the tube or may be friction fitted onto the tube or snapped into a slot or groove formed on the outside of the tube. The flare of shield 17 would not add as much bulkiness to the packaging of the hypodermic syringe as the unfolded disc 16 of FIG. 2. The shield 17, however, similarly could be made of a material similar to that described above to further reduce bulkiness in packaging.

Figure 4:
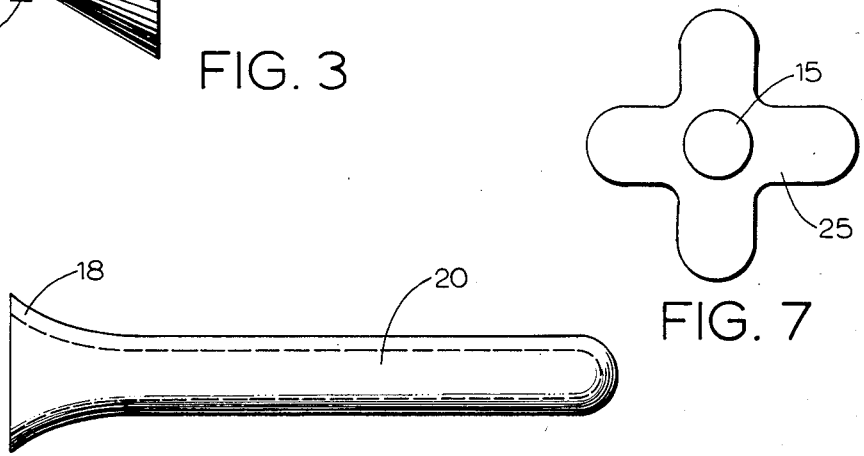
FIG. 4 illustrates yet another embodiment.

Yet another embodiment is illustrated in FIG. 4 which shows a tube 20 having an outwardly forwardly flaring funnel-shaped opening or mouth at 18. Preferably, this would be formed as an integral part of receptacle 20; however, it could be an attachment to tube 15 similar to the previously described embodiments. If the flare were an integral part of the receptacle then the barrel 11 would require a suitable mating tapered surface of some other means would be provided to enable the receptacle to be pushed onto and held by friction at the end of the barrel.

Figure 5:
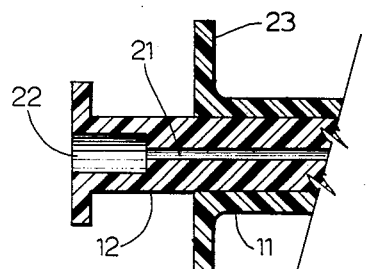
FIG. 5 illustrates still another embodiment.

In the less common case of the needle being separated from the barrel after use, it can be disposed of by inserting it in an elongated opening 21 (FIG. 5) formed at about the axis of plunger 12 contained in barrel 11. Preferably a recess 22 is formed at the outer end of plunger 12 to engage and frictionally hold the holder end 13 of the inserted needle. The flange 23 on the barrel 11 protects the fingers while the needle is being inserted.

Figure 6:
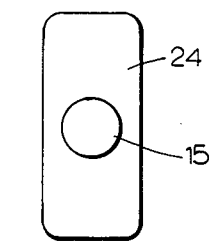
FIG. 6 illustrates yet still another embodiment.
Figure 7:
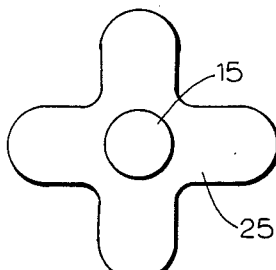
FIG. 7 illustrates a further embodiment.

FIG. 6 is a rear view of a somewhat rectangular shaped shield 24 around tube 15. A shield 25 (FIG. 7) also might be shaped as a cloverleaf or cross.

A further prior art device, which is not shown in the drawing, includes another plastic tube open at both ends covering over the barrel with tube 15 passing through the opening at one end and the additional tube held in place over the barrel by a cap at its other end. When the syringe is to be used the cap is removed and the additional tube is removed and tube 15 is removed. To place the needle back in tube 15 after use and before discarding, the latter is first inserted into the additional tube and the syringe needle is then inserted into tube 15 located at the far end of the additional tube. This is awkward and time-consuming and most nurses find it troublesome to deal with. These difficulties are avoided with the instant invention.

I claim:

1. A safety device for use with a tubular covering having an aperature for a disposable hypodermic syringe, comprising: a finger protecting shield means having a centrally disposed opening for sliding the shield means over the tubular covering, the shield means being flexible and needle puncture resistant, the shield means being removable and is cooperatively held in place proximate the aperature, the shield means extending radially outward for protecting the hand from needle puncture when the tubular covering is held in one hand behind the shield means while the other hand is inserting the needle in the aperature in the tubular covering for disposing the needle after use.

2. The safety device of claim 1, wherein the shield means is held in place by friction.

3. The safety device of claim 1, wherein the shield means is an annular disk.

4. The safety device of claim 1, wherein the shield means is generally rectangular.

5. The safety device of claim 1, wherein the shield means is generally cloverleaf shaped.

6. A safety cover for a hypodermic syringe needle for disposing the needle after it has been used, comprising:
 (a) an elongated tubular covering means having an opening at one end for inserting the sharp end of a syringe needle after it has been used; and
 (b) finger protecting shield means extending radially outward from the covering means adjacent said opening for protecting the user's hand against needle puncture when the sharp end of the needle is being inserted into said opening for disposing the needle, said shield means is an outwardly and forwardly flared needle-guiding rim at the open end of the covering means for guiding the needle into said opening for disposal.

* * * * *